United States Patent [19]

Williams et al.

[11] 4,294,262

[45] Oct. 13, 1981

[54] APPARATUS FOR MONITORING RESPIRATORY PERFORMANCE

[75] Inventors: Garnet M. E. Williams, Edmonton; James E. L. Hollis, Portsmouth, both of England

[73] Assignee: Ferraris Development and Engineering Company Limited, London, England

[21] Appl. No.: 43,772

[22] Filed: May 30, 1979

[30] Foreign Application Priority Data

May 31, 1978 [GB] United Kingdom ............... 25443/78

[51] Int. Cl.³ .............................................. A61B 5/08
[52] U.S. Cl. ..................... 128/726; 73/861.77; 73/861.79
[58] Field of Search ................. 128/726, 725; 73/229, 73/861.77, 861.79, 861.85, 861.91, 861.92, 861.94

[56] References Cited

U.S. PATENT DOCUMENTS

| 3,636,767 | 1/1972 | Duffy ................................... 73/229 |
| 4,030,357 | 6/1977 | Wemyss ............................ 73/229 X |

FOREIGN PATENT DOCUMENTS

| 1302375 | 1/1973 | United Kingdom ................ 128/726 |
| 137624 | 7/1960 | U.S.S.R. ............................. 128/726 |
| 178026 | 11/1964 | U.S.S.R. ............................. 128/726 |
| 185436 | 10/1966 | U.S.S.R. ............................. 128/726 |
| 503132 | 2/1976 | U.S.S.R. ............................... 73/229 |

Primary Examiner—Lee S. Cohen
Attorney, Agent, or Firm—Edwin E. Greigg

[57] ABSTRACT

A respirometer comprises a casing in which a circular chamber is formed. A rotor is mounted for rotation within the chamber and comprises vanes carried by a spindle. A circular wall of glass ceramic material closes an end of the chamber. A pair of aligned radial arms are carried by the spindle between the vanes and the circular wall. Each arm carries a samarium cobalt magnet and rotates with the spindle within a recess in the circular wall. One of the magnets has its north pole adjacent the circular wall and the other has its south pole adjacent the circular wall. A bistable Hall effect sensor is mounted on the opposite side of the circular wall from the rotor with its sensitive region in as close proximity to the rotational path of the magnets as dimensional accuracy will allow. The frequency of change in magnitude of the electrical potential output signal from the sensor is indicative of the rotational speed of the rotor spindle which in turn is indicative of the volume of air or gas flow through the chamber.

6 Claims, 2 Drawing Figures

APPARATUS FOR MONITORING RESPIRATORY PERFORMANCE

CROSS REFERENCE TO RELATED PRIOR ART

Cox, L. A.; Almeida, A. P.; Robinson, J. S.; and Horsely, J. K., "An Electronic Respirometer", British Journal of Anaesthesia, Vo. 46, pages 302 to 310 (1974). Proceedings of the 1st United Kingdom Conference on Permanent Magnets, their manufacture and applications. Edited by Dr. A. G. Clegg, Revised Edition; Magnet Centre, Physics Division, Sunderland Polytechnic, Chester Road, Sunderland, SR1 3SD, (June 1980).

None of the above, whether taken and viewed singly or in combination with each other, are believed to have a bearing on the patent ability of any claim of this invention.

BACKGROUND OF THE INVENTION

This invention relates to apparatus for monitoring respiratory performance comprising a pneumatic to electric transducer which is adapted to actuate an electronic read out unit, the transducer including a rotor which comprises vanes which are carried by a rotor spindle for rotation with the spindle about the axis of the spindle and an electric output signal generator which is coupled non-mechanically with the rotor in a manner which results in the read out being a function of rotation of the spindle. Such apparatus will be referred to hereinafter as "Apparatus of the kind described".

Various forms of non-mechanical coupling have been proposed and of these an optical coupling arrangement incorporating photo electric devices has been preferred so far. One disadvantage of this optical coupling arrangement is the need to replace light bulbs from time to time. Another disadvantage is that it is difficult to isolate the output signal generator from the respiratory gas flow that drives the rotor. An object of this invention is to provide another form of apparatus of the kind described which can be arranged so that it does not suffer from these disadvantages.

SUMMARY AND OBJECTS OF THE INVENTION

According to this invention there is provided apparatus of the kind described, wherein at least one magnet is mounted for rotation with rotation of the rotor spindle and the electric output signal generator comprises a magnetic field sensitive device which senses the magnetic field established by the or each magnet as that magnet travels passed it with rotation of the spindle and which emits an output signal in response to the sensing of such a magnetic field whereby an output indicative of the rotation of the spindle can be derived from the output signals emitted by the device.

Preferably the magnetic material from which the or each magnet is formed is a rare earth magnetic material such as samarium cobalt.

The preferred form of magnetic field sensitive device is a Hall effect sensor.

The rotor may be mounted for rotation within a chamber through which the respiratory gas flow that drives the rotor is passed, the chamber having a wall formed by a non-magnetizable material which extends between the magnetic field sensitive device and the rotor whereby the magnetic field sensitive device is physically isolated from the chamber. Conveniently a circular recess is formed in the surface of the wall of non-magnetizable material that bounds the chamber and the or each magnet is received within that recess as it rotates with rotation of the rotor, the magnetic field sensitive device being mounted on the opposite side of said wall in close proximity to the path of rotation of the or each magnet within the recess. There may be two or more such magnets.

BRIEF DESCRIPTION OF THE DRAWINGS

One embodiment of this invention will be described now by way of example with reference to the accompanying drawings, of which.

DETAILED DESCRIPTION OF THE PREFERRED EMBODIMENT

Figure 1:
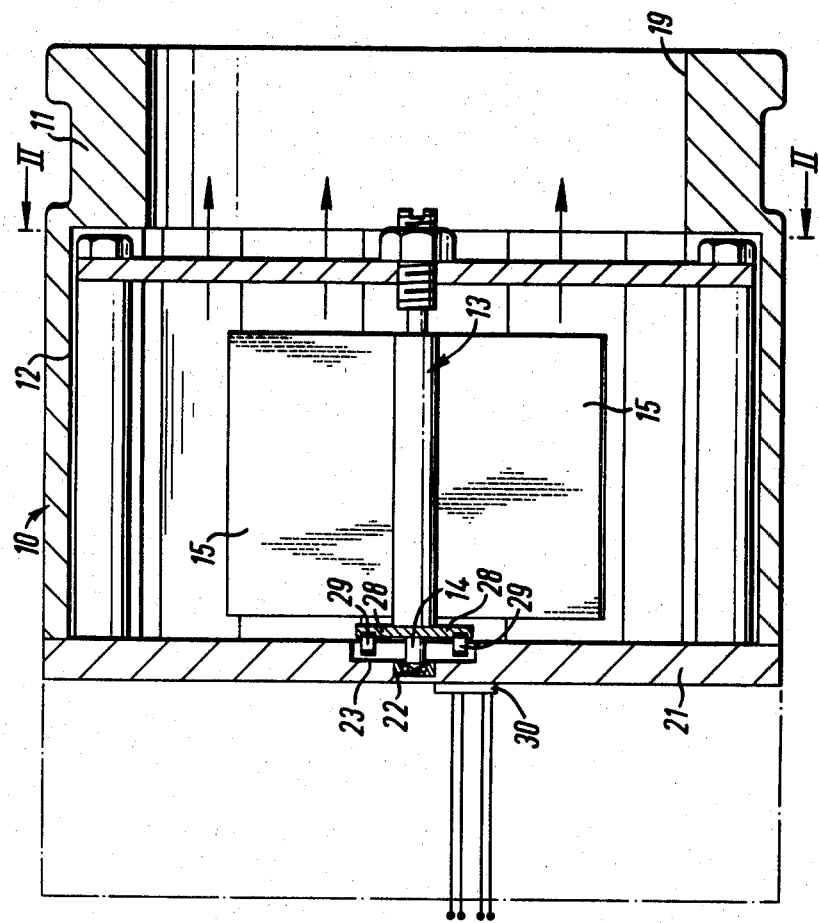
FIG. 1 is a sectioned side view of a respirometer with parts omitted for convenience.
Figure 2:
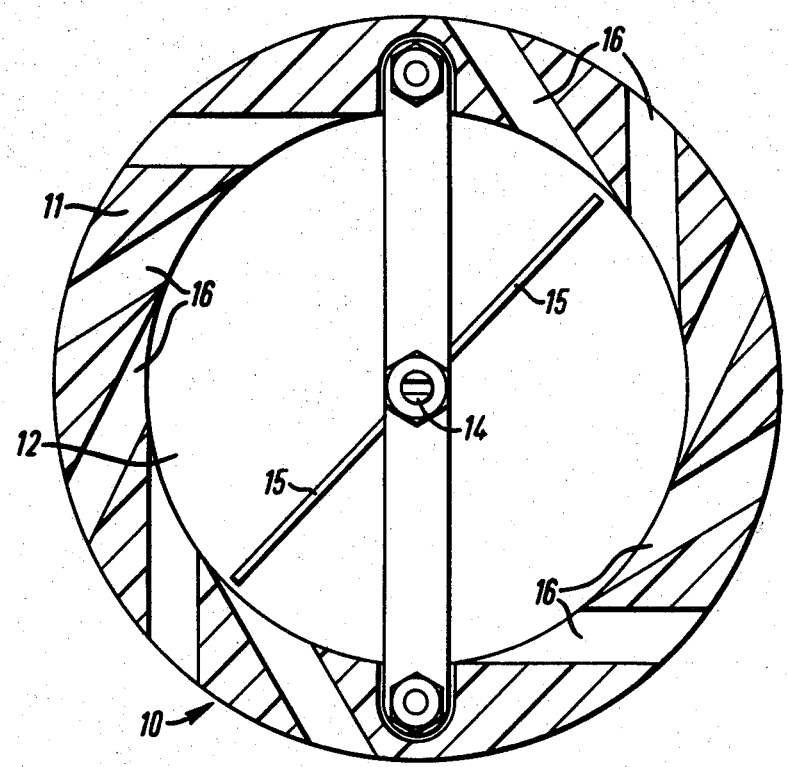
FIG. 2 is a section on the line II—II of FIG. 1.

The drawings show a respirometer 10 which comprises a casing 11 in which a circular chamber 12 is formed. A rotor 13 is mounted for rotation within the chamber 12 and comprises a rotor spindle 14 which is supported within the casing 11 for rotation about its axis, and two axial vanes 15 of titanium foil which are fitted to the rotor spindle 14 and which extend radially from the spindle 14. A circumferential array of inlet ports or slots 16 are formed in the casing 11. A respiratory gas stream to be measured is directed through the inlet ports 16 which are arranged so that the air or gas follows a spiral path within the chamber 12 and impinges on the vanes 15. The respiratory gas is exhausted from the casing 11 axially through an exhaust port 19.

A circular end wall 21 of a machinable glass ceramic material (e.g. Corning MACOR glass ceramic Code 9658), or other suitable machinable non-magnetizable material closes the end of the chamber 12 remote from the exhaust port 19. The adjacent end of the rotor spindle 14 is journaled in a support 22 which is formed at the centre of the wall 21. A recess 23 is formed in the surface of the wall 21 around the support 22. A pair of arms 28 project radially from the end of the spindle 14 between the vanes 15 and the end wall 21. The arms 28 are aligned with one another. Each arm 28 carries a respective permanent magnet 29 at a point on the respective arm remote from the rotational axis of the rotor spindle 14. Each manet 29 is a samarium cobalt magnet and projects into the recess 23, there being a minimal clearance between each magnet 29 and the wall 21. One of the magnets 29 is orientated so that its north pole is at its end adjacent to the end wall 21 and its south pole is at its other end which is the end nearer to the vanes 15. The other magnet 29 is orientated the other way round so that its south pole is at its end nearest to the end wall 21 and its north pole is at its other end which is nearer to the vanes 15.

A Hall effect sensor 30 is mounted on the wall 21 with its sensitive region in as close proximity to the rotational path of the magnets 29 as dimensional accuracy will allow and is on the opposite side of the wall 21 from the magnets 29. The sensor 30 is packaged in non-magnetic material and is connected into an electric circuit which supplies the sensor 30 with electric current to operate it. The sensor 30 is a bistable device which has one state in which its output is a high electrical potential and another state in which its output is a low electrical potential; and is adapted to be switched from one state to the other by being subjected to a magnetic field of one polarity and to be switched from that other state to the first mentioned state by being subjected to a magnetic field of the opposite polarity. The electric circuit is actuatable by the output signal from the sensor 30 so as to produce an electrical output signal in a remote indicating device.

The permanent magnets 29 rotate about the axis of the spindle 14 as the rotor spindle 14 is driven for rotation within the casing 11 by respiratory gas flow through the casing 11. The state of the output signal of the sensor 30 is changed each time the magnetic field of one of the two magnets 29 moves in close proximity to the sensor 30. Thus the magnitude of the electrical potential output from the sensor 30 changes twice during each revolution of the rotor. The frequency of change in magnitude of the electrical potential output signal from the sensor 30 is indicative of the rotational speed of the rotor spindle 14. The rotational speed of the rotor spindle 14 gives an indication of the volume of the air or gas that has passed through the chamber 12.

Samarium cobalt has a high magnetic strength per unit volume. This enables very small magnets to be used so that the moment of inertia of the rotor is not altered significantly by the magnets 29 that are mounted on it.

The Hall effect sensor employed should be a very sensitive device and should be able to withstand temperatures of the order of 150° C. to which the respirometer is subjected fo sterilisation purposes. The Hall effect sensor may be part of a packaged device which includes terminals and semi-conductors. A self-relaxing Hall effect sensor may be used instead of the bistable device described above in which case each magnet would be orientated so that its north pole is at its end adjacent the end wall 21 and its south pole is at its other end which is nearer to the vanes 15. The number of Hall effect sensors and permanent magnets provided depend upon the nature of the required output signal. There may be more than two magnets and more than one sensor. Permanent magnets formed from rare earth magnetic materials other than samarium cobalt may be used instead of the samarium cobalt magnets described.

We claim:

1. Respiratory performance monitoring apparatus comprising means forming a chamber having a wall formed by a non-magnetizable material and ports whereby respiratory gas flow to be monitored when the apparatus is being used is passed through said chamber, and a pneumatic-to-electric transducer adapted to actuate an electronic readout unit, the transducer including a rotor mounted rotatably within said chamber so as to be driven by respiratory gas flow through said chamber, at least one rare earth magnet mounted on said rotor, and a sensitive Hall effect sensor mounted outside the chamber on the opposite side of said wall in close proximity to the path of rotation of said at least one magnet within said chamber whereby an output indicative of rotation of the rotor can be derived from output signals emitted by said Hall effect sensor, the Hall effect sensor and the non-magnetizable material of said wall being able to withstand temperatures of the order to which the apparatus is subjected for sterilization purposes.

2. Apparatus according to claim 1, wherein said at least one magnet is a samarium cobalt magnet.

3. Apparatus according to claim 1, wherein a circular recess is formed in the surface of the wall of non-magnetizable material that bounds the chamber and said at least one magnet is received within that recess as it rotates with rotation of the rotor.

4. Apparatus according to claim 3, wherein there are two such magnets.

5. Apparatus according to claim 1, wherein said means comprises a casing having a bore which comprises said chamber, said wall being at one end of said bore, said ports comprising a circumferential array of slots formed in said casing and a further axially-extending port which is formed by the end of the casing remote from said wall, said circumferential array of slots being arranged so that respiratory gas flow through them into the chamber follows a spiral path within the chamber.

6. Apparatus according to claim 1, wherein said chamber includes means that provides for said gas flow therethrough defining a spiral-to-axial flow path.

* * * * *